(12) United States Patent
Shin et al.

(10) Patent No.: US 10,618,934 B2
(45) Date of Patent: Apr. 14, 2020

(54) PEPTIDE COMPOUND, PRODUCTION METHOD THEREFOR, AND USE THEREOF

(71) Applicant: iNtRON Biotechnology, Inc., Gyeonggi-do (KR)

(72) Inventors: Jong Heon Shin, Daejeon (KR); Ki Bong Oh, Seoul (KR); Dong Chan Oh, Seoul (KR); Sang Kook Lee, Seoul (KR); Lijuan Liao, Seoul (KR); Min Jung You, Suwon-si (KR)

(73) Assignee: iNtRON Biotechnology, Inc., Gyeonggi-do (KR)

( * ) Notice: Subject to any disclaimer, the term of this patent is extended or adjusted under 35 U.S.C. 154(b) by 187 days.

(21) Appl. No.: 15/521,222

(22) PCT Filed: Oct. 23, 2015

(86) PCT No.: PCT/KR2015/011281
§ 371 (c)(1),
(2) Date: Nov. 16, 2017

(87) PCT Pub. No.: WO2016/064245
PCT Pub. Date: Apr. 28, 2016

(65) Prior Publication Data
US 2018/0079780 A1 Mar. 22, 2018

(30) Foreign Application Priority Data

Oct. 23, 2014 (KR) .................. 10-2014-0144427
Jul. 3, 2015 (KR) .................. 10-2015-0095365

(51) Int. Cl.
| | | |
|---|---|---|
| C07K 5/02 | (2006.01) | |
| C12R 1/66 | (2006.01) | |
| A61K 31/165 | (2006.01) | |
| A61K 38/06 | (2006.01) | |
| A61K 45/06 | (2006.01) | |
| C12P 21/02 | (2006.01) | |
| A61K 38/00 | (2006.01) | |

(52) U.S. Cl.
CPC .............. *C07K 5/02* (2013.01); *A61K 31/165* (2013.01); *A61K 38/06* (2013.01); *A61K 45/06* (2013.01); *C07K 5/0202* (2013.01); *C12P 21/02* (2013.01); *C12R 1/66* (2013.01); *A61K 38/00* (2013.01)

(58) Field of Classification Search
None
See application file for complete search history.

(56) References Cited

U.S. PATENT DOCUMENTS 7,671,011 B2 3/2010 Shai et al.
8,394,954 B2 3/2013 Kamal et al.

FOREIGN PATENT DOCUMENTS

| JP | 2010-523488 A | 7/2010 |
| KR | 10-2007-0086038 A | 8/2007 |
| WO | WO 2006/110185 A2 | 10/2006 |
| WO | WO 2008/120235 A1 | 10/2008 |
| WO | WO 2008/144747 A2 | 11/2008 |
| WO | 2008/070357 A2 | 12/2008 |

OTHER PUBLICATIONS

Völkert et al., "Synthesis and Biological Activity of Photoactivatable N-Ras Peptides and Proteins", JACS, 2003, 12749-12758 (Year : 2003).*
Völkert et al., "Synthesis and Biological Activity of Photoactivatable N-Ras Peptides and Proteins", JACS, 2003, pp. 12749-12758 (Year: 2003).*
ChemistryViews.org, "Total Synthesis of Asperphenins", Organic Letters/ACS Publications, 2018, 2 pages. (Year: 2018).*
Mathan, S., International and Antimicrobial Activity of *Aspergillus protuberus* SP1 Isolated from Marine Sediments of South Indian Coast, Chinese Journal of Natural Medicines 2011, pp. 286-282.
Ding, Yousong, Genome-Based Characterization of Two Prenylation Steps in the Assembly of the Stephacidin and notoamide Anticancer Agents in a Marine-Derived *Aspergillus* sp., J. Am Chem. Soc. 2010, pp. 12733-12740.
Notice of Allowance corresponding to Korean application No. 10-2015-0095365, dated Mar. 28, 2017, three pages.
International Search Report and Written Opinion corresponding to PCT/KR2015/011281 dated Jan. 7, 2016.
Remsberg et al., Structural Analogues of Smoothened Intracellular Loops as Potent Inhibitors of Hedgehog Pathway and Cancer Cell Growth, "J Med Chem", 2007, 50, 4534-4538.
Schramm et al., Lipopeptides as Dimerization Inhibitors of HIV1 Protease, "Biol. Chem.", May 1999, vol. 380, pp. 593-596.
Chen et al., "A Photo-Cross-Linking Strategy to Map Sites of Protein-Protein Interactions," "Chem. Eur. J.", 2010, vol. 16, pp. 7389-7394.
Chen et al., "Synthesis and Spectroscopic Characterization of Photo-affinity Peptide Ligands to Study Rhodopsin-G Protein Interaction", "Photochemistry and Photobiology", 2006, vol. 84, pp. 831-838.
Mullen et al., "Synthesis of a-factor peptide from *Saccharomyces cerevisiae* and photoactive analogues via Fmoc solid phase methodology," "Bioorganic and Medicinal Chemistry", Nov. 10, 2010, all pages.
EP Patent Application No. 15851785.4, Partial Supplementary European Search Report dated Jun. 11, 2018, all pages.

\* cited by examiner

*Primary Examiner* — Lianko G Garyu
(74) *Attorney, Agent, or Firm* — Kilpatrick Townsend & Stockton LLP

(57) ABSTRACT

Provided are a novel peptide compound, a method of producing the same, and use of the peptide compound. Since the peptide compound has anticancer activity, the peptide compound may be used for the prevention or treatment of cancer.

7 Claims, 11 Drawing Sheets

Specification includes a Sequence Listing.

US 10,618,934 B2

SEQUENCE LISTING

<160> NUMBER OF SEQ ID NOS: 1

<210> SEQ ID NO 1
<211> LENGTH: 572
<212> TYPE: DNA
<213> ORGANISM: Artificial Sequence
<220> FEATURE:
<223> OTHER INFORMATION: 18S rDNA of Aspergillus sp. F452

<400> SEQUENCE: 1

```
tccgtaggtg aacctgcgga aggatcatta ctgagtgcgg gctgcctccg ggcgcccaac      60
ctcccacccg tgactaccta acactgttgc ttcggcgggg agccctctcg ggggcgagcc     120
gccggggact actgaacttc atgcctgaga gtgatgcagt ctgagtctga atatacaatc     180
agtcaaaact ttcaacaatg gatctcttgg ttccggcatc gatgaagaac gcagcgaact     240
gcgataagta atgtgaattg cagaattcag tgaatcatcg agtctttgaa cgcacattgc     300
gccccctggc attccggggg gcatgcctgt ccgagcgtca ttgctgccca tcaagcccgg     360
cttgtgtgtt gggtcgtcgt cccccccccg ggggacgggc ccgaaaggca gcggcggcac     420
cgtgtccggt cctcgagcgt atggggcttt gtcacccgct cgatttaggg ccggccgggc     480
gccagccgac gtctccaacc attttttctt caggttgacc tcggatcagg tagggatacc     540
cgctgaactt aagcatatca ataagcggag ga                                   572
```

PEPTIDE COMPOUND, PRODUCTION METHOD THEREFOR, AND USE THEREOF

TECHNICAL FIELD

The present invention relates to a novel peptide compound, a method of producing the same, and use of the novel peptide compound.

BACKGROUND ART

Physiologically active substances derived from microorganisms have been a source of antibiotics, antifungal agents, and anticancer drugs, and have been developed as new drugs for treatment of various diseases or become templates for development of new drugs. Examples of antibiotics derived from microorganisms are amphotericin, erythromycin, streptomycin, tetracycline, and vancomycin. In addition, deptomycin isolated from streptomyces which is an actinomyces was approved as a next-generation antibiotic by (FDA) in 2013. Examples of anticancer drugs originated from microbes are doxorubicin, bleomycin, mithramycin, neocarzinostatin, pentostatin, and epothilone. As such, research on physiologically active substances derived from bacteria is very important in the development of antibacterial agents, antifungal agents, and antifungal agents.

To screen physiologically active substances that are structurally different from existing substances, one strategy of the recent studies is to research natural products in a geographically and phylogeneticlly specific environment. Although readily accessible soil microorganisms and land plants have been extensively studied for natural products over a long period of time, studies on microorganisms or marine origin have been relatively inactively done. Oceans cover about 70% of the surface of the earth, and the ocean itself is presented as a space of opportunity that is mostly unexplored. Although the diversity of marine microorganisms is not exactly identified, there has been little research in this area so far that only 1% of marine microorganisms are believed to be cultured or identified.

Therefore, in consideration of the development of structurally new antibiotics and anticancer drugs, it is necessary to select marine microorganisms producing useful physiologically active substances, and to explore and develop new compounds producing such marine microorganisms.

As such, new strains were discovered while selecting and studying new marine fungi. In addition, while studying the new strain, it was found that the new strain is capable of producing a new peptide compound which is also accordingly found to exhibit anticancer activity, thereby completing the present invention.

DETAILED DESCRIPTION OF THE INVENTION

Technical Problem

The provided is a novel peptide compound, and an isomer, a derivative, or a pharmaceutically acceptable salt of the peptide compound isomer of the peptide compound.

In addition, the provided is a strain F452 of *Aspergillus* species producing the peptide compound.

In addition, the provided is a method of producing the peptide compound.

In addition, the provided is a pharmaceutical composition for preventing or treating cancer, the pharmaceutical composition including the peptide compound.

In addition, the provided is a method of preventing or treating cancer.

Technical Solution

According to an aspect, there is provided a novel peptide compound including a lipopeptide and a benzophenone, or an isomer, a derivative, or a pharmaceutically acceptable salt of the peptide compound.

According to another aspect, there is provided a strain F452 of *Aspergillus* sp. producing the peptide compound.

According to another aspect, there is provided a method of producing the peptide compound.

According to another aspect, there is provided a pharmaceutical composition comprising the peptide compound or the isomer, the derivative, or the pharmaceutically acceptable salt of the peptide compound.

According to another aspect, there is provided a method of preventing or treating cancer, the method using the peptide compound or the derivative, or the pharmaceutically acceptable salt of the peptide compound.

Advantageous Effects of the Invention

A new peptide including a lipopeptide and a benzophenone has anticancer activity, and thus, can be used for the prevention or treatment of various cancer types. In addition, a low-priced mass culture medium can be used to provide a high yield of the peptide compound.

BEST MODE

Figure 1A:
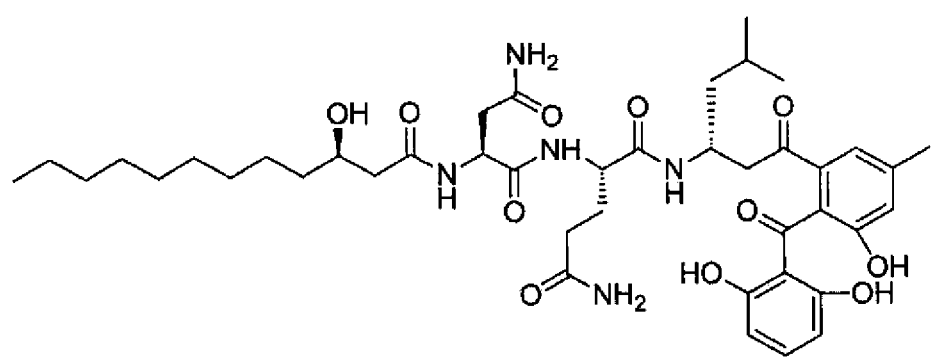
FIGS. 1A and 1B show structure formulas of Asperphenin A and Asperphenin B, respectively.
Figure 1B:
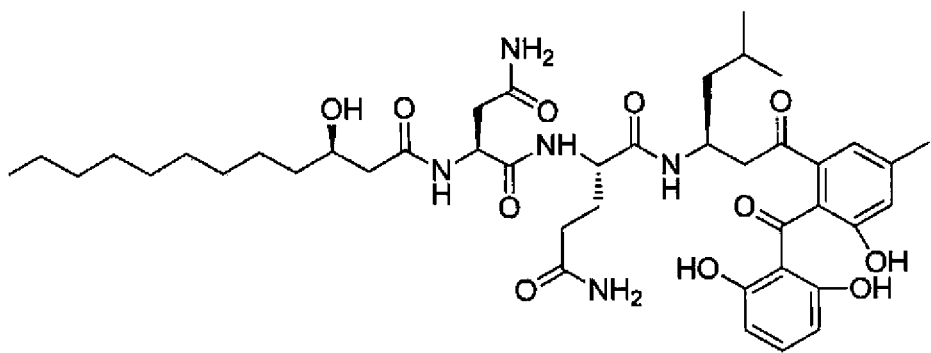
Figure 2:
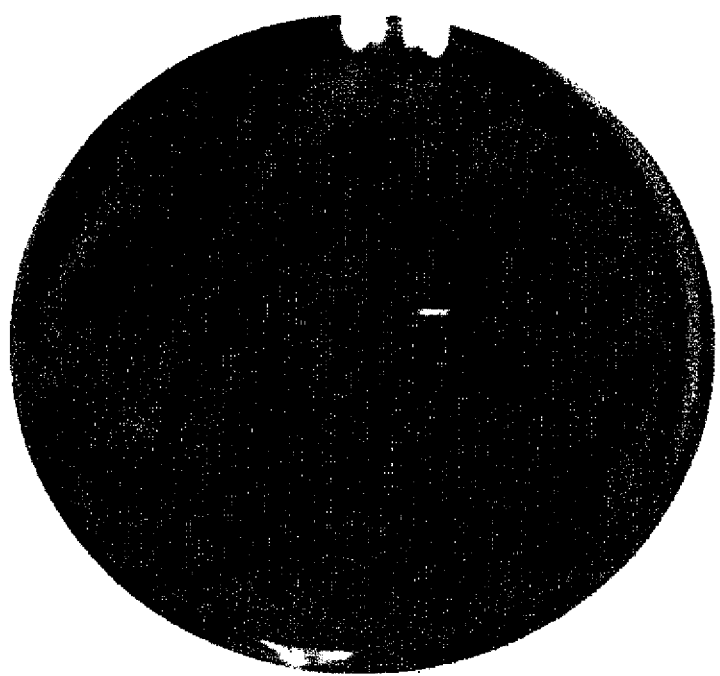
FIG. 2A is an image showing a medium culturing a strain F452 of the genus of *Aspergillus*.

An aspect of the present invention provides a peptide compound including a lipopeptide and a benzophenone, or an isomer, a derivative, or a pharmaceutically acceptable salt of the peptide compound.

The term "peptide compound" as used herein refers to a compound including a peptide. A peptide is a compound in which two or more amino acids are linked by a peptide bond between a carboxyl group of one amino acid and an amino group of another amino acid. Depending on the number of amino acids constituting a peptide, the peptide may be a dipeptide, a tripeptide, a tetrapeptide, or the like. A peptide having about 10 or less peptide bonds is called an oligopeptide, and a peptide having multiple peptide bonds is called a polypeptide.

The term "isomer" as used herein refers to a compound with the same molecular formula as another molecule, but with different link or spacial arrangement of constituent atoms in the molecule. The isomer may include, for example, a structural isomer and a stereoisomer.

The term "derivative" as used herein refers to a compound obtained by substituting a part of the structure of a compound with another or an atomic group.

The term "pharmaceutically acceptable salt" as used herein refers to an inorganic salt and an organic addition salt of a compound.

The term "lipopeptide" as used herein refers to a substance including a lipid connected to a peptide. The lipopeptide may include a lipid connected to a peptide by an amide bond. The amide bond is also referred to as a peptide bond, and is a covalent bond in which an amino group of one molecule and a carboxyl group of another molecule are linked.

The lipid may be a substituted or unsubstituted $C_1$-$C_{20}$ alkyl group, a substituted or unsubstituted $C_2$-$C_{20}$ alkenyl group, or a substituted or unsubstituted $C_2$-$C_{20}$ alkynyl group. The alkyl group may be a $C_2$-$C_{20}$ alkyl group, a $C_5$-$C_{20}$ alkyl group, or a $C_{10}$-$C_{15}$ alkyl group. The alkyl group may include 12 carbons. The alkenyl group may be a $C_2$-$C_{20}$ alkenyl group, a $C_5$-$C_{20}$ alkenyl group, a $C_{10}$-$C_{20}$ alkenyl group, or a $C_{10}$-$C_{15}$ alkenyl group. The alkynyl group may be a $C_2$-$C_{20}$ alkynyl group, a $C_5$-$C_{20}$ alkynyl group, a $C_{10}$-$C_{20}$ alkynyl group, or a $C_{10}$-$C_{15}$ alkynyl group. The expression "substituted" as used herein refers means that a hydrogen atom in an organic compound is substituted with another atomic group to form a derivative. Here, a "substituent" is the atomic atom introduced thereto. The substituent may be, for example, a hydroxyl group, a halogen atom, a $C_1$-$C_{20}$ alkyl group, a $C_2$-$C_{20}$ alkenyl group, a $C_2$-$C_{20}$ alkynyl group, a $C_1$-$C_{20}$ heteroalkyl group, a $C_6$-$C_{20}$ aryl group, a $C_6$-$C_{20}$ arylalkyl group, a $C_6$-$C_{20}$ heteroaryl group, or a $C_6$-$C_{20}$ heteroarylalkyl group, a nitro group, a cyano group, an amino group, an amidino group, a hydrazine group, a hydrazone group, a carboxyl group or a salt thereof, a sulfonic acid or a salt thereof, or a phosphoric acid or a salt thereof.

The peptide may include two, three, or four or more amino acids. The peptide may be, for example, a tripeptide including three amino acids. The peptide may include, for example, N terminal-Asparagine (Asp)-Glutamine (Gln)-Leucine (Leu)-C terminal. The peptide may include one or more beta (β)-amino acids. An amino acid may include an amino group, a carboxyl group, and a side chain specific to the amino acid. 20 types of standard biological amino acids have an amino group linked to a carbon of a carboxyl group, whereas β-amino acids have an amino group linked to β carbon of a carboxyl group. β-amino acids of which side chains are linked to carbons next to amines are $β^3$-amino acids, and β-amino acids of which side chains are linked to carbons next to carboxyl groups are $β^2$-amino acids. The β-amino acid may be β-leucine. The β-amino acid may be $β^3$-leucine.

The benzophenone may be a diphenylmethanone which is an organic compound having a formula of $(C_6H_5)_2CO$. The benzophenone may be, for example, a compound substituted with 1, 2, or 3 or more hydroxyl groups. For example, the benzophenone may be a compound of which at least one selected from $5^{th}$ carbon, $9^{th}$ carbon, and $13^{th}$ carbon is substituted with a hydroxyl group.

The lipopeptide and the benzophenone may be linked via a ketone linkage. For example, the benzophenone may be linked to a C-terminal end of the lipopeptide.

The peptide compound may be represented by Formula 1:

[Formula 1]

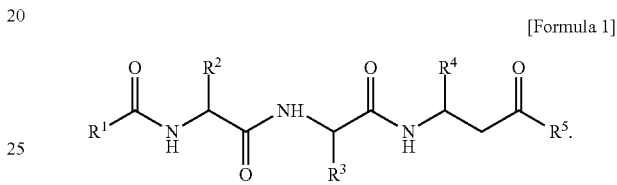

In Formula 1, $R^1$ may be substituted or unsubstituted $C_1$-$C_{20}$ alkyl group, a substituted or unsubstituted $C_1$-$C_{20}$ alkenyl group, or a substituted or unsubstituted $C_1$-$C_{20}$ alkynyl group, wherein $R^1$ may be selectively unsubstituted or substituted with a hydroxyl group, $R^2$, $R^3$, and $R^4$ may each independently be selected from hydrogen, a hydroxyl group, a halogen group, a cyano group, $-C(=O)R_a$, $-C(=O)OR_a$, $-OCO(OR_a)$, $-C=N(R_a)$, $-SR_a$, $-S(=O)R_a$, $-S(=O)_2R_a$, $-PR_a$, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ heteroaryl group, or a combination thereof, and $R^5$ may be a substituted or unsubstituted benzophenone.

The alkyl group, the alkenyl group, the alkynyl group, and the substitution, and the benzophenone are the same as described above.

The peptide compound may be a compound represented by Formula 2:

[Formula 2]

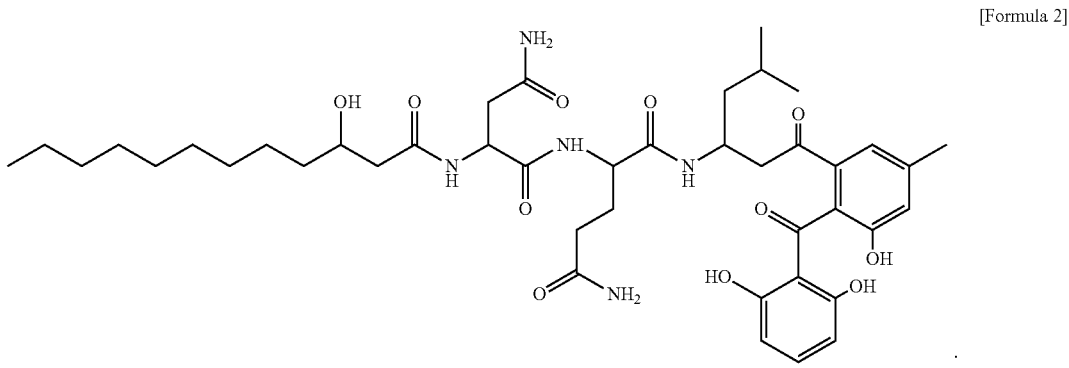 [SMILES: CCCCCCCCCC(O)CC(=O)NC(CC(N)=O)C(=O)NC(CCC(N)=O)C(=O)NC(CC(=O)c1cc(C)cc(O)c1C(=O)c1c(O)cccc1O)CC(C)C]

The compound represented by Formula may be a compound represented by Formula 3 or 4, or an isomer, a derivative, or a pharmaceutically acceptable salt thereof:

[Formula 3]

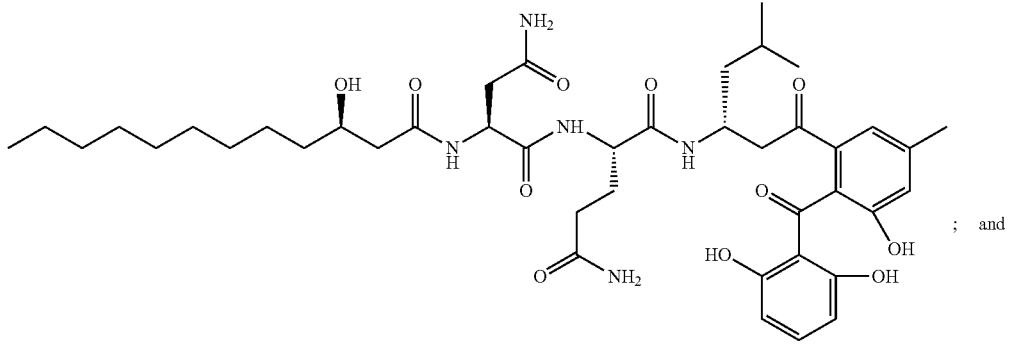

; and

[Formula 4]

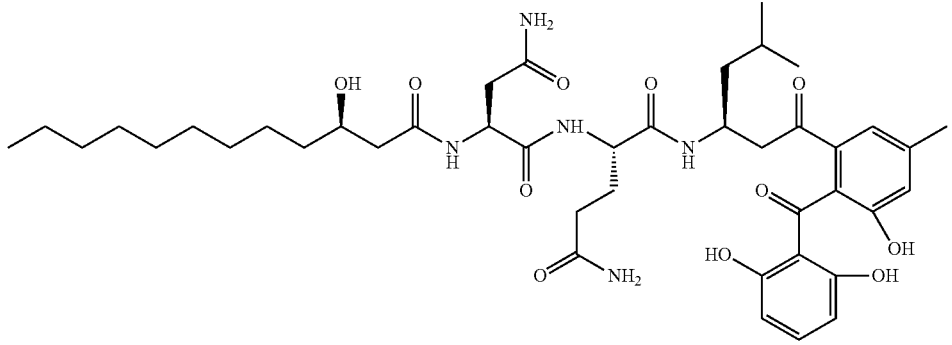

An aspect of the present disclosure provides a strain F452 of *Aspergillus* sp. (Accession Number: KCTC12688BP), the strain producing a peptide compound including a lipopeptide and a benzophenone.

The lipopeptide, the benzophenone, and the peptide compound are the same as described above.

The strain may include a mutant thereof. The mutant may be, for example, caused by a natural mutant or an artificial mutant. The artificial mutant may be caused by a physical mutagen, such as an ultraviolet ray, or a chemical mutagen, such as base compound.

The strain may include its pore, fungus body, bacterial call, or culture.

The strain may be separated or derived from marine sediments.

An aspect of the present disclosure provides a method of producing a peptide compound including a lipopeptide and a benzophenone, the method including culturing a strain F452 (Accession Number: KCTC12688BP) of *Aspergillus* sp. to prepare a culture medium; and separating a peptide compound including a lipopeptide and a benzophenone from the culture medium.

The method may include culturing the strain F452 of *Aspergillus* sp. (Accession Number: KCTC12688BP) to prepare a culture medium.

The strain F452 of *Aspergillus* sp. is the same as described above.

The culturing may be culturing a strain in a liquid medium or a solid medium.

The medium may include instant ocean. The medium may include carbon sources, such as glucose, rice, starch syrup, dextrin, starch, molasses, animal oils, or plant oils. The medium may include nitrogen sources, such as yeast extracts, peptones, wheat bran, soybean oil meal, wheat, malt, cottonseed meal, fish scrap, corn steep liquor, meat juice, ammonium sulfate, sodium nitrate, or urea. The medium may include, if necessary, table salt, potassium, magnesium, cobalt, chlorine, phosphoric acid, sulfuric acid, or inorganic salt that stimulates production of other ions. The medium may include, for example, instant ocean, yeast extracts, peptones, and rice.

The culturing may be shake culture or stationary culture that is performed under aerobic conditions. The temperature at which the culturing is performed may be, for example, in a range of about 20° C. to about 37° C. or about 25° C. to about 30° C., or may be 27° C. The time required for the culturing may be, for example 1 day to 2 months, 1 week to 2 months, 2 weeks to 2 months, 1 month to 2 months, or 6 weeks.

The method may include separating a peptide compound from the culture medium, the peptide compound including a lipopeptide and a benzophenone.

The lipopeptide, the benzophenone, and the peptide compound are the same as described above.

The separating of the peptide compound from the culture medium may include performing concentration, centrifugation, filtration, or chromatography on the culture medium. For example, the culture medium may be extracted with ethylacetate, water, or a combination thereof. The obtained concentrate may be divided by chromatography, into 8 fractions depending on polarity. The chromatography may be, for example, reverse phase flash chromatography using, for example, water, acetonitrile, or a combination thereof as a mobile phase. The fractions may be fractioned by using the reverse phase flash chromatography, to thereby obtain 8 fractions.

Among the obtained fractions, fractions eluted with a water/acetonitrile mixed solution, which is mixed at a volume ratio of 50:50, may be capable of separating the peptide compound by using high performance liquid chromatography (HPLC). The HPLC uses a water/methanol mixed solution, which is mixed at a volume ratio of 70:30, as a mobile phase, and may be performed by using reversed-phase semi-preparative HPLC. The separated peptide compound may have purity of about 80%, about 90%, or about 99% or more.

An aspect of the present disclosure provides a pharmaceutical composition for preventing or treating cancer, the pharmaceutical composition including a peptide compound including a lipopeptide and a benzophenone, or an isomer, a derivative, or a pharmaceutically acceptable salt of the peptide compound.

The lipopeptide, the benzophenone, the peptide compound, the isomer, the derivative, and the pharmaceutically acceptable salt are the same as described above.

The cancer may include, for example, intrahepatic cholangiocarcinoma, liver cancer, thyroid cancer, colon cancer, testis cancer, myelodysplastic syndrome, glioblastoma, oral cavity cancer, mycosis fungoides, acute myeloid leukemia, chronic myeloid leukemia, acute lymphoblastic leukemia, chronic lymphoblastic leukemia, base cell carcinoma, ovarian epithelial cancer, ovarian germ cell tumor, male breast cancer, brain tumor, pituitary adenoma, multiple myeloma, gallbladder cancer, biliary tract cancer, colon cancer, retinoblastoma, choroid melanoma, ampullar of vater cancer, bladder cancer, peritoneal cancer, parathyroid carcinoma, adrenal gland cancer, non-small cell lung cancer, tongue cancer, astroma, small cell lung cancer, pediatric brain tumor, pediatric lymphoma, pediatric leukemia, small bowel neoplasm, meningioma, esophageal cancer, glioma, neuroblastoma, renal pelvis and ureter cancer, kidney cancer, malignant soft tissue tumor, malignant bone tumor, malignant lymphoma, malignant mesothelioma, malignant melanoma, ocular tumor, pudendum cancer, urethral tumor, carcinoma of unknown primary origin, gastric lymphoma, stomach cancer, gastric carcinoid tumor, gastrointestinal stromal tumor, Willms tumor, breast cancer, sarcoma, penile carcinoma, pharynx cancer, gestational trophoblastic disease, cervical cancer, endometrial cancer, sarcoma of uterus, prostate cancer, metastatic brain tumor, rectal cancer, rectal carcinoid tumor, vaginal cancer, spinal tumor, vestibular schwannoma, pancreatic cancer, salivary gland tumor, tonsillar cancer, squamous cell carcinoma, adenocarcinoma of lung, lung cancer, squamous cell carcinoma of lung, skin cancer, anal cancer, larynx cancer, or a combination thereof. The cancer may be, for example, lung cancer, colon cancer, stomach cancer, liver cancer, or breast cancer.

The term "prevention" as used herein refers to any action that inhibits diseases or delays onset by administration of a composition. The term "treatment" as used herein refers to any action that improves or alleviates a symptom of a disease by the administration of a composition.

The pharmaceutical composition may further include a known active ingredient having anticancer activity. Such a known active ingredient may be an anticancer drug. The anticancer drug may be irinotecan, 5-fluotouracil, gemcitabine, etoposide, paclitaxel, or a combination thereof. When the anticancer drug is further included, the pharmaceutical composition may be a single composition or an individual composition.

The pharmaceutical composition may further include a carrier, an excipient, or a diluent. Such a carrier, an excipient, or a diluent may be, for example, lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, or mineral oil.

The pharmaceutical composition may be formulated in the form of oral preparations such as powders, granules, tablets, capsules, suspensions, emulsions, and syrups, aerosols, external preparations, suppositories, or sterilized injection solutions, according to a conventional method. In the case of formulation, a diluent or an excipient, such as a filler, an extender, a binder, a wetting agent, a disintegrant, and a surfactant, that are typically used may be used.

Regarding the pharmaceutical composition, solid preparations for oral administration may be tablets, pills, powders, granules, or capsules. The solid preparations may further include an excipient. Such an excipient may be, for example, starch, calcium carbonate, sucrose, lactose, or gelatin. In addition, the solid preparations may further include a lubricant, such as magnesium stearate or talc. Regarding the pharmaceutical composition, liquid preparations for oral use may be suspensions, solutions, emulsions, or syrups. The liquid preparations may include water or liquid paraffin. The liquid preparations may include an excipient, such as a wetting agent, a sweetening agent, an air freshener, or a preservative. Regarding the pharmaceutical composition, formulations for parenteral administration may be sterilized aqueous solutions, non-aqueous solutions, suspensions, emulsions, lyophilized agents, or suppositories. Non-aqueous solutions or suspensions may include vegetable oils or esters. Vegetable oils may include, for example, propylene glycol, polyethylene glycol, or olive oil. Esters may include, for example, ethyl oleate. A base of the suppository may be witepsol, macrogol, tween 61, cacao paper, laurin, or glycerogelatin.

An aspect of the present discloser provides a method of preventing or treating cancer, the method including administering a pharmaceutical composition for preventing or treating cancer into an individual, the pharmaceutical composition including a peptide compound including a lipopeptide and a benzophenone, or an isomer, a derivative, or a pharmaceutically acceptable salt of the peptide compound.

The lipopeptide, the benzophenone, the peptide compound, the isomer, the derivative, the pharmaceutically acceptable salt, cancer, prevention, treatment, and the pharmaceutical composition are the same as described above.

The individual may be a mammal including a rat, a mouse, a dog, a cow, a monkey, and a human being.

A preferred dosage of the peptide compound varies depending on the conditions and weight of a patient, a degree of disease, drug form, and administration route and time, but may be appropriately selected by one of ordinary skill in the art. However, the peptide compound may be, for example, administered in an amount of about 0.0001 mg/kg to about 100 mg/kg, or about 0.001 mg/kg to about 100 mg/kg, once or several times a day. The peptide compound in the pharmaceutical composition may be included in an amount of about 0.0001 wt % to about 10 wt % or about 0.001 wt % to about 1 wt %, based on the total weight of the total composition.

The pharmaceutical dosage forms of the peptide compound may be in the form of a pharmaceutically acceptable salt of the peptide compound. The peptide compound may be used alone or in combination with other pharmaceutically active compound.

The pharmaceutical composition may be administered in a variety of routes to a mammal including a rat, a mouse, a dog, a cow, a horse, a monkey, and a human being. An administration method may be, for example, oral, rectal or intravenous, intramuscular, subcutaneous, intrauterine, or intra-cerebroventricular injections.

The method may further include administering an anticancer drug into an individual. The peptide compound, its isomer, derivative, or pharmaceutically acceptable salt, and the anticancer drug may be administered simultaneously, individually, or sequentially. For example, the anticancer drug may be administered into the individual after the administration of the peptide compound or the isomer, the derivative, or the pharmaceutically acceptable salt of the peptide compound into the individual.

Hereinafter, the present disclosure will now be described more fully with reference to the accompanying Examples below. However, these Examples are for illustrative purposes only, and should not be construed as being limited to the scope of the inventive concept in any way.

Example 1. Isolation and Identification of Asperphenin a and Asperphenin B 1-1. Isolation of Strain F452 of *Aspergillus* Species (*Aspergillus* sp.)

In order to screen a strain producing a substance having anticancer activity, a strain F452 was isolated from tropical marine sediments. The whole genome of the strain F452 was isolated, and an 18S ribosomal DNA sequence was cloned by using a polymerase chain reaction (PCR). The nucleic acid sequence of the 18S ribosomal DNA was analyzed (SEQ ID NO: 1).

As a result of the nucleic acid sequence analysis, the strain F452 was identified as a novel strain that was systematically similar to *Aspergillus versicolor*. The strain F452 was named as strain F452 of *Aspergillus* sp., and then, deposited at the Depositary Authority on Oct. 13, 2014 (Accession Number: KCTC12688BP).

1-2. Culture of Strain F452 of *Aspergillus* sp.

The strain F452 of *Aspergillus* sp. was inoculated into a sterilized YPG solid medium (5 g of yeast extract, 5 g of peptone, 10 g of glucose, 16 g of agar, and 24.8 g of INSTANT OCEAN® (Aquarium systems) per 1 L of distilled water), and then, was subjected to primary culture at a temperature of 27° C. for several days.

The strain F452 cultured in the solid medium of the primary culture was inoculated into a sterilized YPG liquid medium (5 g of yeast extract, 5 g of peptone, 10 g of glucose, and 24.8 g of INSTANT OCEAN® (Aquarium systems) per 1 L of distilled water), and then, was subjected to second culture at a temperature of 27° C. for 7 days while being shaken at 150 rpm.

10 ml of the second culture was inoculated into a solid rice medium (200 g of rice (Organica Co., Ltd., Icheon Rice, Gyeonggi-do), 2.5 g of yeast extract, 2.5 g of peptone, 12.4 g of INSTANT OCEAN® (Aquarium systems) per 500 ml of distilled water), and then, was subjected to third culture at a temperature of 27° C. for 6 weeks.

1-3. Isolation and Purification of Asperphenin a and Asperphenin B

The solid medium of the third culture in which strain F452 was cultured in Example 1-2 was obtained, and then, 1 L of ethylacetate (Daejung Chemicals & Metals Co., Ltd.) was immersed in every 100 g of the obtained solid medium for 1 day. Such a procedure was repeated three times in total. Ethylacetate thus obtained was filtered through a filter paper (Advantec), and the filtrate was decompressed, to thereby remove ethylacetate which was a solvent. Such a procedure was repeated to obtain 25 g of a crude extract. 200 ml of methanol (Daejung Chemicals & Metals Co., Ltd.) was added to the crude extract, and then, the methanol layer was decompressed, to thereby obtain 11.4 g of a methanol extract. The methanol extract thus obtained was divided into 8 fractions according to reversed phase chromatography (MERCK, C18, 700 g, reversed-phase). An eluent used in 5 fractions was used by reducing water by 5% from a water/acetonitril (Burdick & Jackson) solution mixed at a volume ratio of 60:40. The final fraction was divided using 100% methanol (Daejung Chemicals & Metals Co., Ltd.), acetone (Daejung Chemicals & Metals Co., Ltd.), and ethylacetate (Daejung Chemicals & Metals Co., Ltd.), to thereby obtain fractions.

Fraction 3 divided using a water/acetonitril solution mixed at a volume ratio of 50:50 was analyzed according to liquid chromatography (LC)-mass spectrometry (MS) and based on hydrogen nuclear resonance spectrum. To identify the compositions of the fractions, LC/MS using Agilent 1200 Series LC (Agilent technologies) and 6130 Series MS was used. Here, the mass spectrum was obtained using an LTQ-Orbitrap ESI-MS mass spectrometer manufactured by Thermo-Finnigan Company, and was represented in a mass-to-charge (m/z) form. According to the analysis on the LC-MS and the hydrogen nuclear resonance spectrum, it was confirmed that the culture medium of the strain contained a novel secondary metabolite, which was to be named as Asperphenin.

Fraction 3 was isolated using $C_{18}$ reversed-phase semi-preparative HPLC (particle diameter of 5 µm, 250 mm×10 mm (length×inner particle diameter), elution rate of 2 ml/min) with a refractive index (RI) detector (Shodex). A mobile phase used for the isolation was a water/methanol solution mixed at a volume ratio of 70:30, and the reversed-phase semi-preparative HPLC was performed for about one and half an hour. Accordingly, 50.0 mg of Asperphenin A and 46.0 mg of Asperphenin B were obtained.

1-4. Physicochemical Characterization Analysis of Asperphenin A and Asperphenin B Asperphenin A and Asperphenin B were in a pale yellow, stable at room temperature, and well dissolved in a moderate organic solvent, such as methanol and acetone. The structures of Asperphenin A and Asperphenin B were determined based on nuclear magnetic resonance spectrum, infrared and ultraviolet spectral data, optical rotary power, and high-resolution mass spectrometry data. The nuclear magnetic resonance spectrum ($^1$H NMR, $^{13}$C NMR) was obtained using 500 MHz NMR manufactured by Bruker Company and DMSO-$d_6$ as a solvent. The mass spectrum was obtained using an LTQ-Orbitrap ESI-MS mass spectrometer manufactured by Thermo-Finnigan Company, and was represented in a mass-to-charge (m/z) form. The infrared spectrum was obtained using an FT-IR-4200 spectrometer manufactured by Jasco Company. The ultraviolet spectrum was obtained using an U-3010 UV/VIS spectrometer manufactured by Hitachi Company. The optical rotary power was obtained using a P-1020 polarimeter manufactured by Jasco Company.

The structure positioning of each of Asperphenin A and Asperphenin B by the nuclear magnetic resonance spectrum was as follows in Tables 1 and 2.

[Asperphenin A]
(1) Molecular formula: $C_{42}H_{61}N_5O_{11}$
(2) Molecular weight: 811
(3) Color: Pale yellow
(4) Optical rotary power: −24.7 (c 1.0, methanol, 25° C.)
(5) Infrared absorption band (neat): 3309, 1671 wavenumbers
(6) $^1$H-NMR (DMSO-$d_6$, 600 MHZ): see Table 1
(7) $^{13}$C-NMR (DMSO-$d_6$, 150 MHZ): see Table 1

TABLE 1

Chemical shift values of nuclear magnetic resonance spectrum of Asperphenin A

| Position | $\delta_C$ | Type | $\delta_H$ | mult (J in Hz) |
|---|---|---|---|---|
| 1 | 136.0 | C | | |
| 2 | 120.4 | CH | 7.21 | s |
| 3 | 138.5 | C | | |
| 4 | 120.4 | CH | 6.84 | s |
| 5 | 153.4 | C | | |
| 6 | 128.6 | C | | |
| 7 | 201.8 | C | | |
| 8 | 111.1 | C | | |
| 9 | 161.6 | C | | |
| 10 | 106.8 | CH | 6.19 | d (8.3) |
| 11 | 135.7 | CH | 7.15 | t (8.3) |
| 12 | 106.8 | CH | 6.19 | d (8.3) |
| 13 | 161.6 | C | | |
| 14 | 20.8 | $CH_3$ | 2.29 | s |
| 15 | 198.3 | C | | |
| 16 | 44.7 | $CH_2$ | 3.00 | dd (16.5, 4.5) |
| | | | 2.85 | dd (16.5, 8.7) |
| 17 | 43.4 | CH | 4.13 | m |
| 17-NH | | | 7.66 | d (8.3) |
| 18 | 42.5 | $CH_2$ | 1.28 | m |
| | | | 0.98 | ddd (13.7, 9.4, 3.4) |
| 19 | 24.1 | CH | 1.45 | m |
| 20 | 21.3 | $CH_3$ | 0.66 | d (6.7) |
| 21 | 23.3 | $CH_3$ | 0.71 | d (6.7) |
| 22 | 170.2 | C | | |
| 23 | 52.6 | CH | 4.02 | m |
| 23-NH | | | 7.92 | d (7.7) |
| 24 | 27.6 | $CH_2$ | 1.87 | m |
| | | | 1.65 | m |
| 25 | 31.4 | $CH_2$ | 2.02 | t (7.9) |
| 26 | 173.9 | C | | |
| 26-$NH_2$ | | | 7.14 | br s |
| | | | 6.70 | br s |
| 27 | 170.9 | C | | |
| 28 | 49.8 | CH | 4.44 | m |
| 28-NH | | | 8.04 | d (7.5) |
| 29 | 36.9 | $CH_2$ | 2.40 | m |
| 30 | 171.8 | C | | |
| 30-$NH_2$ | | | 7.39 | br s |
| | | | 6.91 | br s |
| 31 | 171.2 | C | | |
| 32 | 43.7 | $CH_2$ | 2.18 | m |
| 33 | 67.5 | CH | 3.75 | m |
| 33-OH | | | 4.59 | brs |
| 34 | 37.0 | $CH_2$ | 1.30 | m |
| 35 | 25.1 | $CH_2$ | 1.30 | m |
| | | | 1.19 | m |
| 36 | 31.3 | $CH_2$ | 1.19 | m |
| 37 | 29.1 | $CH_2$ | 1.19 | m |
| 38 | 29.1 | $CH_2$ | 1.19 | m |
| 39 | 29.0 | $CH_2$ | 1.19 | m |
| 40 | 28.7 | $CH_2$ | 1.19 | m |
| 41 | 22.1 | $CH_2$ | 1.21 | m |
| 42 | 13.9 | $CH_3$ | 0.81 | t (7.0) |

[Asperphenin B]
(1) Molecular formula: $C_{42}H_{61}N_5O_{11}$
(2) Molecular weight: 811
(3) Color: Pale yellow
(4) Optical rotary power: −18.4 (c 1.0, methanol, 25° C.)
(5) Infrared absorption band (neat): 3309, 1671 wavenumbers
(6) $^1$H-NMR (DMSO-$d_6$, 600 MHZ): see Table 2
(7) $^{13}$C-NMR (DMSO-$d_6$, 150 MHZ): see Table 2

TABLE 2

Chemical shift values of nuclear magnetic resonance spectrum of Asperphenin B

| Position | $\delta_C$ | Type | $\delta_H$ | mult (J in Hz) |
|---|---|---|---|---|
| 1 | 136.0 | C | | |
| 2 | 120.3 | CH | 7.21 | s |
| 3 | 138.6 | C | | |
| 4 | 120.5 | CH | 6.84 | s |
| 5 | 153.4 | C | | |
| 6 | 128.7 | C | | |
| 7 | 201.8 | C | | |
| 8 | 111.1 | C | | |
| 9 | 161.6 | C | | |
| 10 | 106.8 | CH | 6.19 | d (8.1) |
| 11 | 135.7 | CH | 7.14 | t (8.1) |
| 12 | 106.8 | CH | 6.19 | d (8.1) |
| 13 | 161.6 | C | | |
| 14 | 20.8 | $CH_3$ | 2.29 | s |
| 15 | 198.4 | C | | |
| 16 | 44.6 | $CH_2$ | 2.97 | dd (16.4, 4.2) |
| | | | 2.83 | dd (16.4, 8.5) |
| 17 | 43.5 | CH | 4.13 | m |
| 17-NH | | | 7.63 | d (8.2) |
| 18 | 42.6 | $CH_2$ | 1.34 | m |
| | | | 1.01 | m |
| 19 | 24.2 | CH | 1.46 | m |
| 20 | 21.4 | $CH_3$ | 0.69 | d (6.4) |
| 21 | 23.4 | $CH_3$ | 0.74 | d (6.4) |
| 22 | 170.4 | C | | |
| 23 | 52.7 | CH | 4.02 | m |
| 23-NH | | | 8.03 | d (8.4) |
| 24 | 27.5 | $CH_2$ | 1.87 | m |
| | | | 1.65 | m |
| 25 | 31.5 | $CH_2$ | 2.02 | m |
| 26 | 174.1 | C | | |
| 26-$NH_2$ | | | 7.16 | br s |
| | | | 6.74 | br s |
| 27 | 171.0 | C | | |
| 28 | 49.9 | CH | 4.46 | ddd (6.9, 6.9, 5.1) |
| 28-NH | | | 8.05 | d (5.1) |
| 29 | 37.0 | $CH_2$ | 2.53 | dd (15.6, 6.9) |
| | | | 2.42 | dd (15.6, 6.9) |
| 30 | 171.9 | C | | |
| 30-$NH_2$ | | | 7.41 | br s |
| | | | 6.95 | br s |
| 31 | 171.3 | C | | |
| 32 | 43.7 | $CH_2$ | 2.18 | m |
| | | | 2.18 | m |
| 33 | 67.5 | CH | 3.75 | m |
| 33-OH | | | 4.60 | brs |
| 34 | 37.0 | $CH_2$ | 1.30 | m |
| 35 | 25.1 | $CH_2$ | 1.30 | m |
| | | | 1.19 | m |
| 36 | 31.3 | $CH_2$ | 1.19 | m |
| 37 | 29.1 | $CH_2$ | 1.19 | m |

TABLE 2-continued

Chemical shift values of nuclear magnetic resonance spectrum of Asperphenin B

| Position | $\delta_c$ | Type | $\delta_H$ | mult (J in Hz) |
|---|---|---|---|---|
| 38 | 29.1 | $CH_2$ | 1.19 | m |
| 39 | 29.0 | $CH_2$ | 1.19 | m |
| 40 | 28.8 | $CH_2$ | 1.19 | m |
| 41 | 22.1 | $CH_2$ | 1.22 | m |
| 42 | 14.0 | $CH_3$ | 0.81 | t (6.7) |

The structure of each of Asperphenin A and Asperphenin B analyzed on the basis of the nuclear magnetic resonance spectrum was represented by a chemical formula below.

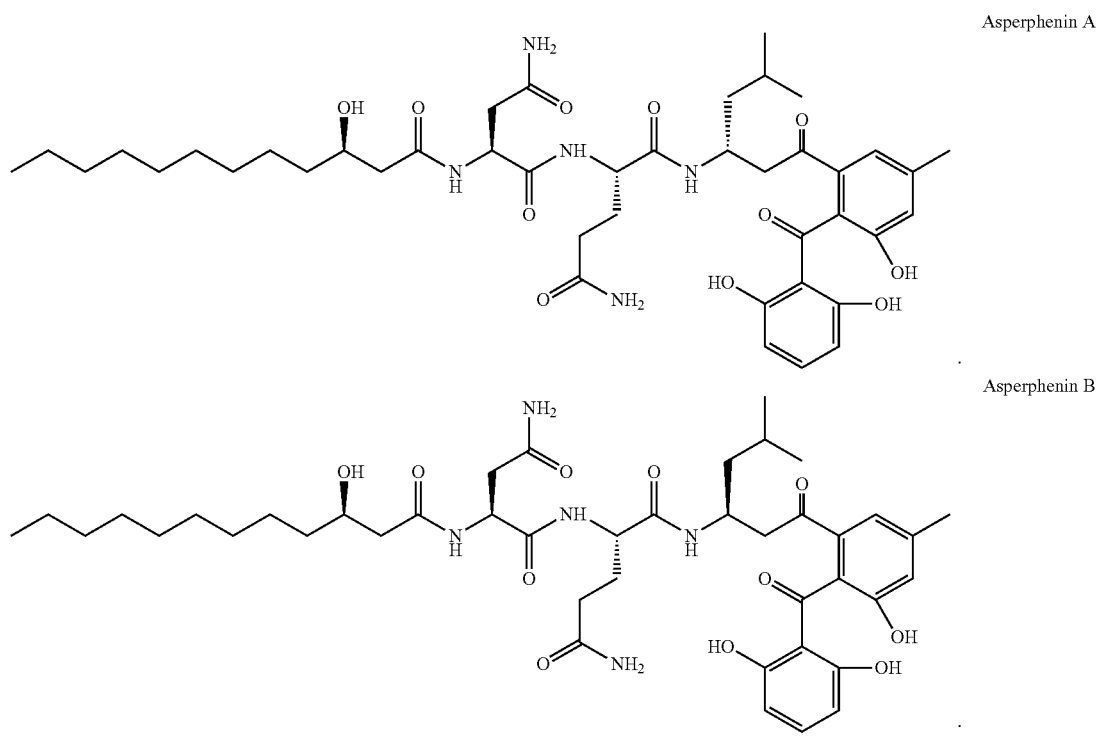

Asperphenin A

Asperphenin B

Example 2. Anticancer Activity of Asperphenin A and Asperphenin B

2-1. Verification of Anticancer Activity of Asperphenin A and Asperphenin B Regarding a lung cancer cell line A549 (Korean Cell line Bank), a colon cancer cell line HCT116 (ATCC), a stomach cancer cell line SNU638 (Korean Cell Line Bank), a liver cancer cell line SK-HEP-1 (Korean Cell line Bank), and a breast cancer cell line MDA-MB-231 (Korean Cell line Bank), a sulforhodamine B (SRB) assay which is a method of measuring cell viability was used for measuring apoptosis effects of Asperphenin.

In detail, 190 μl of a cell suspension at a concentration of $3.5 \times 10^4$ cells/ml was inoculated in each well of a 96-well microplate. 0.8 μM, 4 μM, 20 μM, or 100 μM of Asperphenin was added to the cell culture medium, and cultured at a temperature of 37° C. for 72 hours under the condition of 5% $CO_2$. After incubation, 50 μl of 50% (v/v) trichloroacetic acid solution (Sigma Aldrich) was added to each well, and then, incubated at a temperature of 4° C. for 30 minutes, to thereby fix the cells thereto. The fixed cells were washed with water five times, and then, dried in the air.

Next, 80 μl of a 0.4% (w/v) SRB aqueous solution (Sigma Aldrich) containing 1% (v/v) acetic acid (DUKSAN) was added to each well, incubated at room temperature for 1 hour to stain cells therein, and the stained cells washed with water and dried. The cells were dissolved by adding 200 μl of 10 mM Tris (pH 10.0) (Sigma Aldrich) to each well, and then, the number of living cells was calculated by measuring the absorbance thereof at 515 nm. The concentration of the compound inhibiting cell growth to 50% based on the number of the living cells, i.e., 50% inhibition concentration ($IC_{50}$) was calculated, and the results are shown in Table 3. Here, as a positive control, etoposide (Sigma Aldrich) was used.

TABLE 3

Cell growth inhibition concentrations of Asperphenin A and Asperphenin B ($IC_{50}$, μM)

| | A549 | HCT116 | SNU638 | SK-HEP-1 | MDA-MB-231 |
|---|---|---|---|---|---|
| Asperphenin A | 14.6 | 1.7 | 5.8 | 2.3 | 3.1 |
| Asperphenin B | 41.8 | 2.6 | 11.7 | 3.0 | 6.0 |
| Etoposide | 0.7 | 1.9 | 0.8 | 0.6 | 10.6 |

As shown in Table 3, Asperphenin A exhibited strong cell inhibition effects against the cell lines of lung cancer, colon cancer, stomach cancer, and breast cancer. Asperphenin B exhibited strong cell inhibition effects against the cell lines of colon cancer, stomach cancer, liver cancer, and breast cancer, except for the cell line A549. In particular, Asperphenin A and Asperphenin B both exhibited similar anticancer activity to or better anticancer activity against the colon cancer cell line HCT116 than that of etoposid which is a positive control.

2-2. Verification of Anticancer Activity of Asperphenin B Against Colon Cancer Cell Line As shown in Table 3, it was confirmed whether Asperphenin B had cell growth inhibition effects against not only the colon cancer cell line HCT116, but also other colon cancer cell lines.

From the colon cancer cell lines HCT116 (ATCC), HCT15 (Korean Cell Line Bank), LS174T (Korean Cell Line Bank), RKO(ATCC), and SW480(ATCC), cell growth inhibition concentrations ($IC_{50}$, μM) were calculated as described in Example 2-1, and the results are shown in Table 4. Here, as a positive control, paclitaxel (Sigma Aldrich) was used.

TABLE 4

Growth inhibition value of cancer cell against Asperphenin B ($IC_{50}$)

|  | HCT15 | HCT116 | LS174T | RKO | SW480 |
|---|---|---|---|---|---|
| Asperphenin B (μM) | 7.20 | 4.05 | 1.84 | 1.17 | 31.35 |
| Paclitaxel (nM) | >100 | 0.42 | 0.46 | 0.21 | >100 |

As shown in Table 4, Asperphenin B strongly inhibited the cell growth of 4 colon cancer cell lines, except for the cell line SW480, and more particularly, Asperphenin B exhibited the strongest inhibitory effects against the cell line RKO.

2-3. Measurement of Cell Cycle Change in Colon Cell Line by Asperphenin B

The effects of Asperphenin B on the cell cycle of the colon cancer cell line RKO was confirmed by flow cytometry.

RKO cells (ATCC) were diluted in a medium containing 10% (v/v) FBS to become 1×10$^5$ cells/ml, and then, inoculated into a 60 mm culture dish. The inoculated cells were cultured for about 24 hours at a temperature of 37° C. under the condition of 5% $CO_2$. The cultured cells were washed with phosphate-buffered saline (PBS) once, and the medium was replaced by a fresh medium. Asperphenin B at the final concentration of 0.625 μM, 1.25 μM, 2.5 μM, 5 μM, or 10 μM was added to the cultured cells, and then, the cells were cultured at a temperature of 37° C. under condition of 5% $CO_2$.

After a certain period of time, cells attached to the culture dish and cells not attached to the medium were collected. The collected cells was washed with PBS once, and then, 1 ml of cold 70% (v/v) ethanol. The cells were incubated at a temperature of 4° C. for about 12 hours to fix the cells. After removing 70% (v/v) ethanol, the fixed cells were washed with PBS once. 500 μl of RNase A (Sigma Aldrich) at a concentration of 50 μg/ml as added to the cells, and the cells were incubated at room temperature for about 30 minutes. Propidium iodide (PI) at a final concentration of 50 μg/ml was added to the cells, and then, the cells were incubated at room temperature for about 30 minutes in a condition where reactants were in the shaded state. The cells stained with PI were subjected to analysis of cell cycle by using a BD FACSCalibur flow cytometer (manufactured by BD Biosciences). Based on the flow cytometry results, cell ratios at the sub-$G_1$, $G_0/G_1$, S, and $G_2/M$ phases were calculated. Here, as a negative control, cells to which Asperphenin B was not added was used.

Figure 3A:
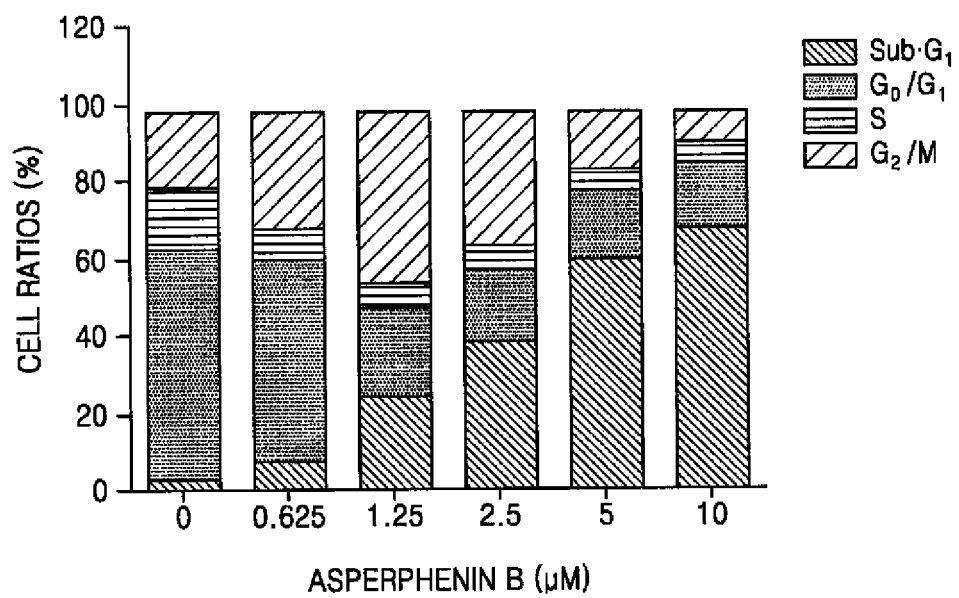
FIG. 3A is a graph showing RKO cell ratios (%) of each cell cycle according to the concentration of Asperphenin B.
Figure 3B:
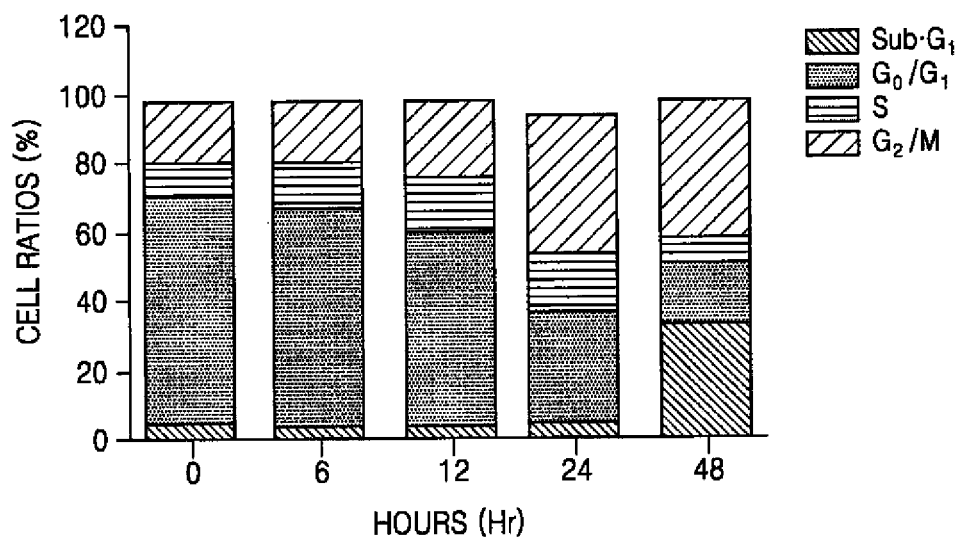
FIGS. 3B and 3C are each a graph showing RKO cell ratios (%) of a cell cycle according to the incubation time of Asperphenin B at a concentration of 2.5 µM and 5 µM.
Figure 3C:
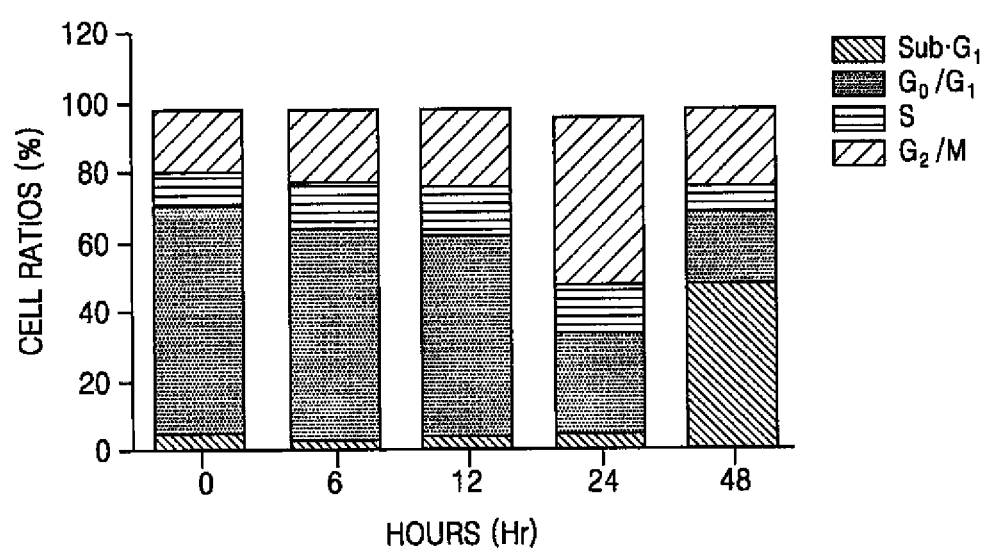

When the RKO cells were incubated for 48 hours in the presence of Asperphenin B, cell ratios (%) dependent on the concentration of Asperphenin B are shown in FIG. 3A and Table 5. When the RKO cells were incubated in the presence of Asperphenin B at the concentrations of 2.5 μM and 5 μM, cell ratios (%) dependent on the incubation time are shown in FIGS. 3B and 3C, and Table 6.

TABLE 5

| Cell cycle phase | Asperphenin B concentrations | | | | | |
|---|---|---|---|---|---|---|
|  | 0 μM (negative control) | 0.625 μM | 1.25 μM | 2.5 μM | 5 μM | 10 μM |
| Sub-$G_1$ | 3.03% | 7.14% | 24.18% | 38.60% | 59.90% | 67.82% |
| $G_0/G_1$ | 59.69% | 52.49% | 23.02% | 17.99% | 17.59% | 17.07% |
| S | 14.85% | 8.11% | 6.39% | 6.63% | 5.29% | 5.46% |
| $G_2/M$ | 20.50% | 29.56% | 43.94% | 34.58% | 15.97% | 8.92% |

TABLE 6

| Cell cycle phase | Control 0 hour | 2.5 μM Asperphenin B | | | | 5 μM Asperphenin B | | | |
|---|---|---|---|---|---|---|---|---|---|
|  |  | 6 hours | 12 hours | 24 hours | 48 hours | 6 hours | 12 hours | 24 hours | 48 hours |
| Sub-$G_1$ | 4.40% | 3.77% | 3.25% | 5.03% | 33.38% | 3.19% | 3.80% | 4.86% | 48.23% |
| $G_0/G_1$ | 66.21% | 62.16% | 56.50% | 30.73% | 17.80% | 60.66% | 57.60% | 28.35% | 20.53% |
| S | 9.70% | 13.82% | 15.09% | 17.38% | 6.55% | 13.48% | 14.63% | 14.08% | 5.90% |
| $G_2/M$ | 17.55% | 18.28% | 22.18% | 40.76% | 39.31% | 20.21% | 20.93% | 48.88% | 23.37% |

As shown in FIG. 3A and Table 5, in the case where the RKO cells and Asperphenin B were incubated for 48 hours, the cells at the sub-$G_1$ phase were increased according to the concentrations of Asperphenin, as compared to the control, whereas the cells at the $G_0/G_1$ and S phases were decreased. The cells in the $G_2/M$ phase were increased as compared to a control in which low-concentrated Asperphenin B was treated, and were decreased as compared to a control in which high-concentrated Asperphenin B was treated. In addition, as shown in FIGS. 3B and 3C, and Table 6, the cells in the sub-$G_1$ and $G_2/M$ phases were changed depending on the treatment time of Asperphenin B. In the case where Asperphenin B at the concentration of 2.5 μM or 5 μM was treated for about 24 hours, the cells in the $G_2/M$ phase increased as compared to a control. In the case Asperphenin B at the concentration of 2.5 μM or 5 μM was treated for about 48 hours, the cells in the $G_2/M$ phase decreased as compared to the case where Asperphenin B at the concentration of 2.5 μM or 5 μM was treated for about 24 hours. The ratio of cells in the sub-$G_1$ phase showing no change for 0 to 24 hours during the treatment of Asperphenin B, increased. It was confirmed that the cells in the $G_2/M$ phase occurred cell cycle arrest until 24 hours of the treatment of Asperphenin B, but after 48 hours of the treatment of Asperphenin B, the cell apoptosis was induced.

2-4. Measurement of Induction of Apoptosis by Asperphenin B

The process of apoptosis in the cell line RKO by Asperphenin B was confirmed using a Annexin V-FITC apoptosis measuring kit (manufactured by D Pharmingen).

As described in Example 2-3, Asperphenin B at the concentration of 0.625 μM, 1.25 μM, 2.5 μM, 5 μM, or 10 μM was added to the RKO cells, cultured for 48 hours to obtain cells. 300 μl of 1× binding buffer was added to the obtained cells, and well mixed together. Then, 5 μl of Annexin V and 5 μl of PI were added to 100 μl of the cell mixture, and allowed to react at room temperature for 15 minutes in the shaded stated. 400 μl of 1× binding buffer was added to the reactants, a FACSCalibur flow cytometer (BD FACSCalibur, BD Biosciences) was used to analyze the cell apoptosis. Based on the flow cytometry results, ratios of cells that were not stained (i.e., living cells), cells stained with annexin V (i.e., cells apoptosized at the early state), cells stained with both PI and annexin V (i.e., cells apoptosized at the late state or cells necrotized,), or cells stained with PI only (i.e., cells necrotized) were calculated. As a negative control, cells to which Asperphenin B was not added were used.

Figure 4:
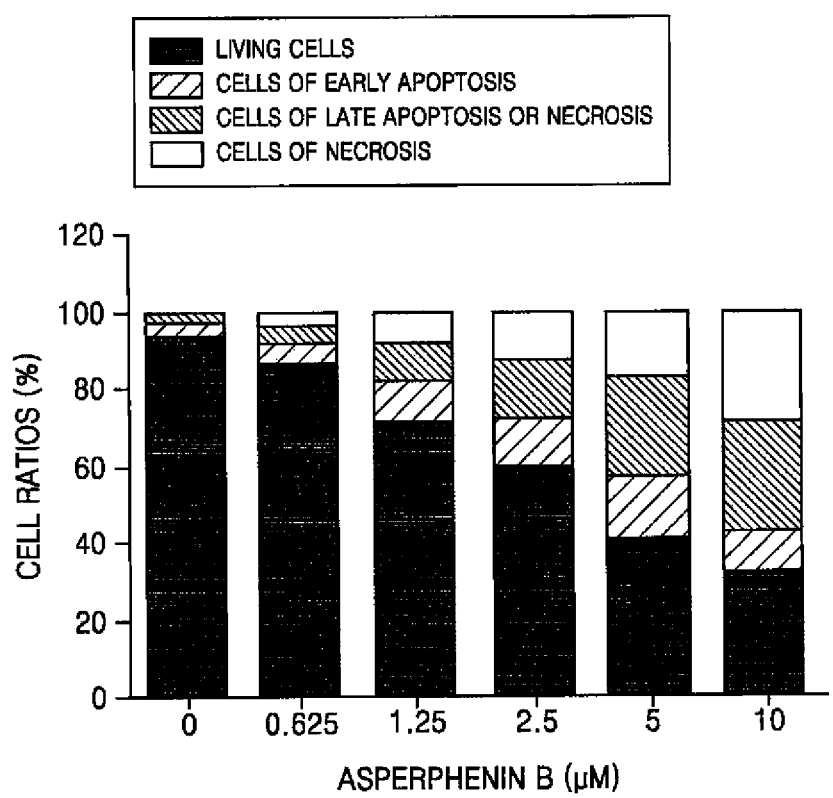
FIG. 4 is a graph showing ratios (%) of living cells, cells of early apoptosis, cells of late apoptosis or necrosis, or cells of necrosis, according to the concentration of Asperphenin B.

When the RKO cells were incubated for 48 hours in the presence of Asperphenin B, cell ratios (%) depending on the concentrations of Asperphenin B are shown in FIG. 4. As shown in FIG. 4, the ratios of the cells of early apoptosis and the cells of late apoptosis or necrosis increased as compared to the ratio of the control. Here, the ratio of necrotic cells was increased as compared to that of the control. Therefore, it was confirmed that Asperphenin B induced apoptosis and necrosis of the RKO colon cancer cell line.

2-5. Evaluation of Effects of Asperphenin B on Cell Cycle-Related Proteins and Apoptosis-Related Proteins As described in Example 2-3, cells were obtained in a way that Asperphenin B at the concentration of 0.625 μM, 1.25 μM, 2.5 μM, 5 μM, or 10 μM was added to the RKO cells, and then, cultured for 48 hours. However, cells were obtained in a way that Asperphenin B at the concentration of 5 μM was added to the RKO cells, and then, cultured for 0 to 48 hours. Then, proteins were obtained from the obtained cells.

Regarding the expression of the cell cycle-related proteins, anti-p-cyclin B1(Ser147) antibody (Cell Signaling Technology), anti-cyclin B1 antibody (Santa Cruz), anti-p-cdc2(Tyr15) antibody (Cell Signaling Technology), anti-cdc2 antibody (Santa Cruz), and anti-β-actin antibody (Santa Cruz) were used to perform immunoblotting thereon. Images obtained by immunoblotting are shown in FIGS. 5A and 5B.

Figure 5A:
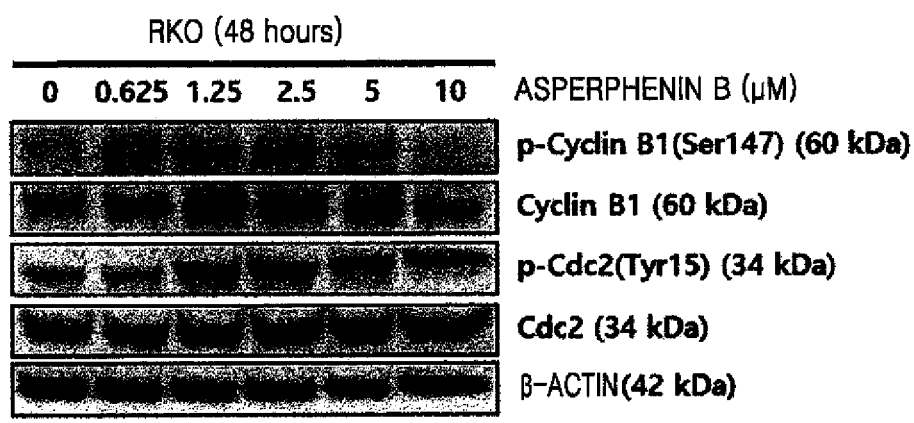
FIGS. 5A and 5B are each an immunoblot image of cell cycle-related proteins according to the concentration of Asperphenin B and the incubation time (in hours) of Asperphenin B at a concentration of 5 µM.
Figure 5B:
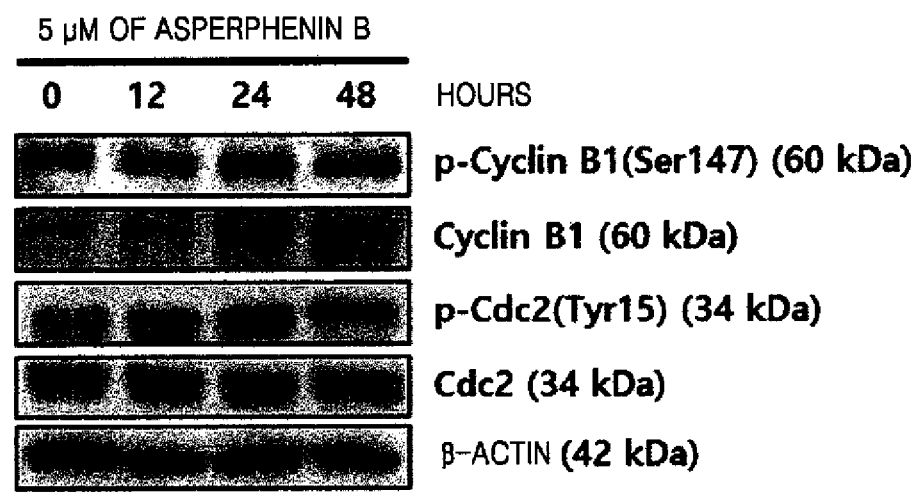

As shown in FIG. 5A, when the RKO cells were incubated for 48 hours in the presence of Asperphenin B, the expression of non-active p-cdc2 (Tyr15) protein was increased in a concentration-dependent manner. The expression of non-active p-cyclin B1 (Ser147) protein was increased in the cells treated with 2.5 μM of Asperphenin B. The expression of p-cyclin B1 (Ser147) protein and cyclin B1 protein decreased in the cells treated with 5 μM and 10 μM of Asperphenin B. In addition, as shown in FIG. 5B, when the cells were treated with 5 μM of Asperphenin B, the expression of p-cdc2 (Tyr15) protein was increased in time-dependent manner, and the expression of p-cyclin B1 (Ser147) was highest at about 24 hours. Therefore, it was confirmed that Asperphenin B regulated the expression of cell cycle-related factors in the RKO colon cancer cells.

Also, regarding the expression of apoptosis-related proteins, anti-ATM antibody (Cell Signaling Technology), anti-p-Chk (Thr68) antibody (Cell Signaling Technology), anti-Chk antibody (Cell Signaling Technology), anti-p-H2AX antibody (Cell Signaling Technology), anti-p53 antibody (Santa Cruz), anti-Bax antibody (Santa Cruz), anti-BID antibody (Cell Signaling Technology), anti-Caspase-8 antibody (Cell Signaling Technology), anti-Caspase-3 antibody (Cell Signaling Technology), anti-Caspase-9 antibody (Cell Signaling Technology), anti-cleaved PARP antibody (BD Biosciences), and anti-β-actin antibody (Santa Cruz) were used, to thereby perform immunoblotting. Images obtained by immunoblotting are shown in FIGS. 6A and 6B.

Figure 6A:
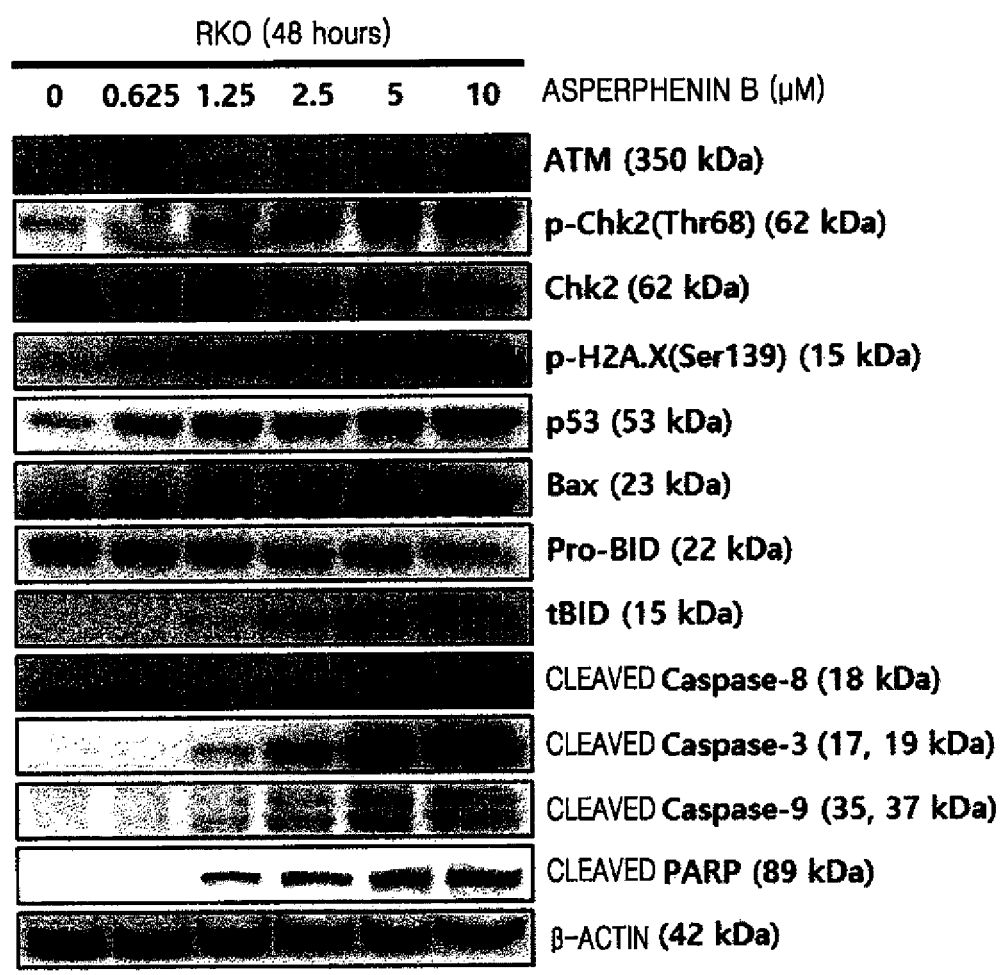
FIGS. 6A and 6B are each an immunoblot image of cell apoptosis-related proteins according to the concentration of Asperphenin B and the incubation time (in hours) of Asperphenin B at a concentration of 5 µM.
Figure 6B:
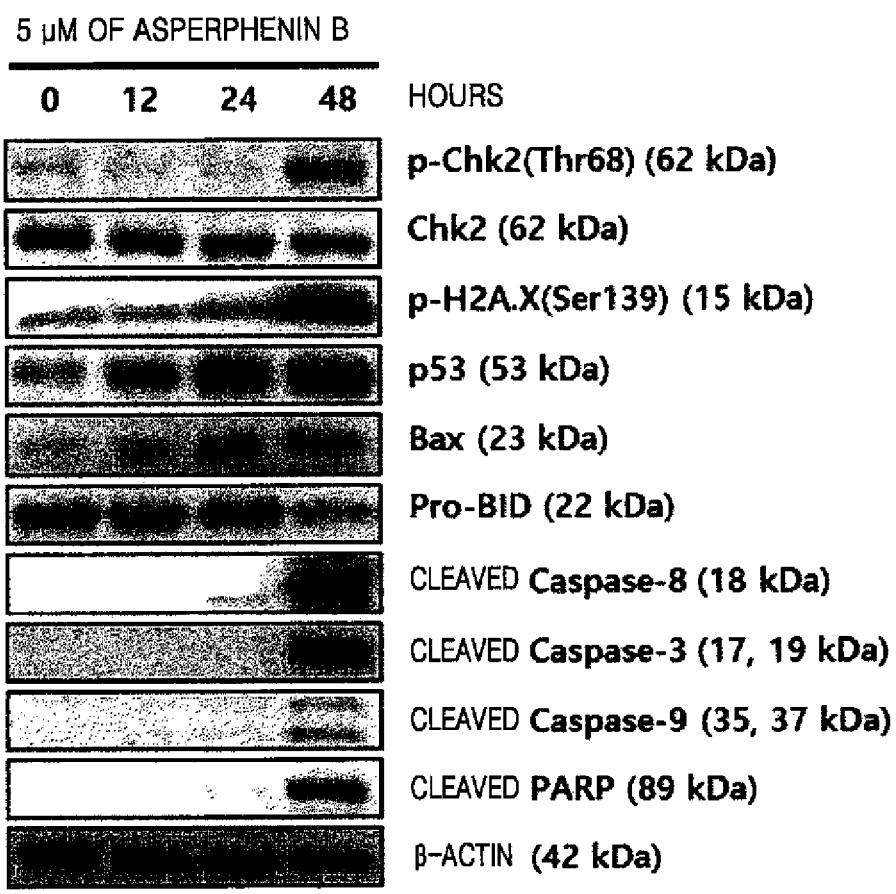

As shown in FIG. 6A, when the RKO cells were incubated for 48 hours in the presence of Asperphenin B, the expression of ATM protein was increased in a concentration-dependent manner while Chk2 and H2AX, which are sub-regulatory factors of ATM proteins, were phosphorylated to be activated. The expression of p53 protein was increased in a concentration-dependent manner, leading to the increased expression of Bax. In addition, the cleavage of poly(ADP-ribose) polymerase (PARP), which is a substrate of Bid, caspase-8, caspase-9, caspase-3, and caspase-3, have been induced by Asperphenin B. As shown in FIG. 6B, when the cells were treated with 5 μM of Asperphenin B, the expression of apoptosis-inducing proteins and marker proteins, such as p-Chk2 (Thr68), p-H2AX (Ser139), cleaved caspase-8, cleaved caspase-9, cleaved caspase-3, and PARP, was increased in a group where the cells were treated for 48 hours. The expression of p53 and Bax was increased in a time-dependent manner. Accordingly, it was confirmed that Asperphenin B regulated the expression of apoptosis-related factors of the RKO colon cancer cells.

2-6. Production of Reactive Oxygen Species (ROS) by Asperphenin B

ROS was capable of inducing apoptosis within a cell, and in this regard, it was examined whether ROS has been produced within a cell by Asperphenin B.

In detail, as described in Example 2-3, Asperphenin B at the concentration of 2.5 μM, 5 μM, or 10 μM wad added to the RKO cells. Cells were collected after the RKO cells were cultured for 24 hours. In addition, a cell group in which 5 mM of N-acetylcysteine (NAC) (Sigma Aldrich), which is an antioxidant, was added to 5 μM and 10 μM of Asperphenin B was prepared as a comparative group, whereas a cell group in which none of Asperphenin B and NAC was contained as a control.

Afterwards, 2',7'-dichlorofluorescin diacetate (DCFH-DA) (Sigma Aldrich) having a final concentration of 20 μM was added to the cell culture medium, and then, cultured at a temperature of 37° C. for 30 minutes under the condition of 5% $CO_2$. Cells attached to the cell medium and cells not attached to the cell medium were all collected, washed with cold PBS twice, and then, suspended again in 1 ml of PBS to measure intensity of 2',7'-dichlorofluorescin (DCF) by using a BD FACSCalibur flow cytometer (manufactured by BD Biosciences). Based on the intensity of DCF, ratios of cells producing ROS were calculated, and results thereof are shown in table 7.

TABLE 7

| Drug | Ratio of cells producing ROS |
| --- | --- |
| No drug treatment (control) | 5.95% |
| 2.5 μM Asperphenin B | 8.14% |
| 5 μM Asperphenin B | 13.86% |
| 10 μM Asperphenin B | 14.26% |

TABLE 7-continued

| Drug | Ratio of cells producing ROS |
|---|---|
| 5 µM Asperphenin B + 5 mM NAC | 1.41% |
| 10 µM Asperphenin B + 5 mM NAC | 2.55% |

As shown in Table 7, when the RKO cells were incubated for 24 hours in the presence of Asperphenin B, the production of ROS increased about 2.4 times as much as the production of ROS in the control. However, the production of ROS by Asperphenin B was inhibited by NAC, which is an antioxidant. Therefore, it was confirmed that Asperphenin B induced the production of ROS in the RKO colon cancer cells.

2-7. Administration of Asperphenin B in Combination with Other Anticancer Drugs

The effects of administration of Asperphenin B in combination with other anticancer drugs were examined in vitro.

Figure 7A:
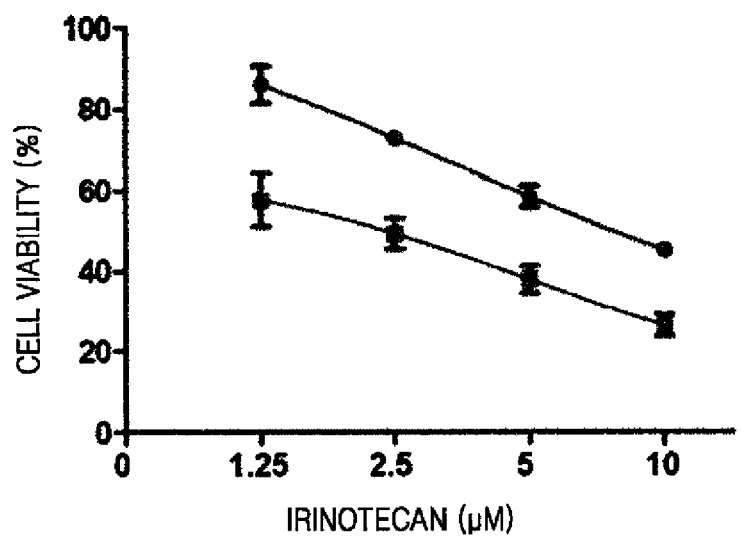
FIGS. 7A to 7C are each a graph showing cell viability (%) of a combination of Asperphenin B and other anticancer drugs, or other anticancer drugs only.
Figure 7B:
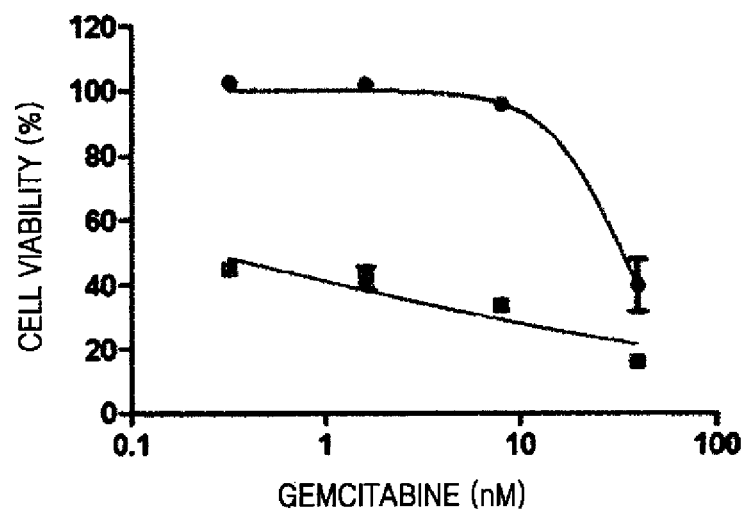
Figure 7C:
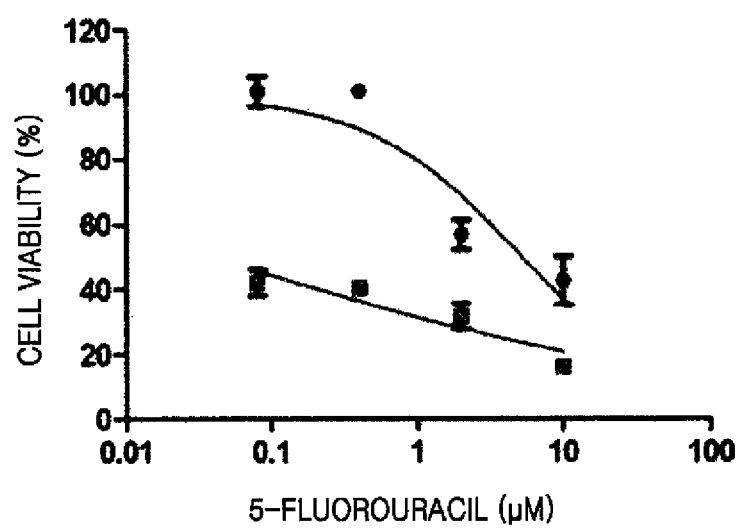

RKO cells diluted in a medium containing 10% (v/v) FBS were inoculated in each well of a 96-well microplate so that each plate included $7 \times 10^3$ cells, and then, the cells were cultured for about 24 hours at a temperature of 37° C. under the condition of 5% $CO_2$. In the medium containing 10% (v/v) FBS, irinotecan (Sigma Aldrich), 5-fluorouracil (Sigma Aldrich), or gemsitabin (Sigma Aldrich) was mixed with Asperphenin B at a ratio of 1:1, and then, the mixture was added to the cultured cells. Then, the cells were cultured for 48 hours at a temperature of 37° C. under the conditions of 5% $CO_2$. The cell viability was measured according to an SRB assay, and the measured cell viability results are shown in FIGS. 7A to 7C. FIG. 7A shows the cell viability (%) in the case using irinotecan only at the concentrations of 1.25 µM to 10 µM (●) and the case using irinotecan and 2.5 µM of Asperphenin B in combination (■). FIG. 7B shows the cell viability (%) in the case using gemsitabin only at the concentrations of 1 nM to 100 nM (●) or the case using gemsitabin and 8 µM of Asperphenin B in combination (■). FIG. 7C shows the cell viability (%) in the case using 5-fluorouracil at the concentrations of 0.1 µM to 10 µM (●) or 5-fluorouracil and 8 µM of Asperphenin B in combination (●).

In addition, the effects of the administration in combination were measured according to Equation 1, and results thereof are shown in Table 8.

Effects of administration in combination=$D1/(Dx)1+D2/(Dx)2$ [Equation 1]

D1: Concentration of Asperphenin B with expected effect in administration in combination D2: Concentration of other anticancer drugs with expected effect in administration in combination (Dx)1: Concentration of Asperphenin B with expected effect in administration of Asperphenin B only (Dx)2: Concentration of other anticancer drugs with expected effect in administration of other anticancer drugs only When the calculated effect of the administration in combination is <1, =1, and >1, it is meant to be synergistic effect, additive effect, and antagonistic effect, respectively.

TABLE 8

| Anticancer drug | Conc. of anticancer drug (µM) | Conc. of Asperphenin B (µM) | Effect of administration in combination | Level symbols representing effect of administration in combination |
|---|---|---|---|---|
| Irinotecan | 1.25 | 2.5 | 0.792 | ++ |
| Irinotecan | 2.5 | 2.5 | 0.751 | ++ |
| | 5 | 2.5 | 0.691 | +++ |
| | 10 | 2.5 | 0.650 | +++ |
| 5-fluorouracil | 0.08 | 8 | 0.863 | + |
| 5-fluorouracil | 0.4 | 8 | 0.852 | + |
| | 2 | 8 | 0.786 | ++ |
| | 10 | 8 | 0.765 | ++ |
| Gemsitabin (µM) | 0.32 | 8 | 0.907 | ± |
| | 1.6 | 8 | 0.882 | + |
| | 8 | 8 | 0.801 | ++ |
| | 40 | 8 | 0.714 | ++ |

As shown in FIGS. 7A to 7C and Table 8, the effects of cell growth inhibition increased in the case where Asperphenin B was administrated in combination, as compared to the case where irinotecan, 5-fluorouracil, or gemsitabin was administered alone.

2-8. Verification of Anticancer Effect of Asperphenin B in Tumor Xenograft Mouse Model The anticancer effect of Asperphenin B was verified in a tumor xenograft mouse model to which human colon cancer cell line was transplanted.

In detail, RKO cells were subcutaneously injected at a concentration of $3.5 \times 10^6$ cells/150 µl into the right side of a nude mouse (Central Lab. Aminol Inc., hairless and small mouse that was tymus free and had dried beard at birth). When the tumor size reached 60 $mm^3$ after 14 days of the injection into the RKO cells, 4 mg/kg or 8 mg/kg of Asperphenin B was administered intraperitoneally 3 times a week, i.e., a total of 21 days (n=5). The tumor size was measured by using a digital caliper for 21 days at intervals of 3 to 4 days. Here, as a control, a nude mouse to which Asperphenin B was not administered was used (n=5).

A tumor volume was calculated according to Equation 2, and a tumor growth inhibition ratio was calculated according to Equation 3 based on the calculated tumor volume.

Tumor volume $(mm^3)$=(length)×(width)×(height)×$\pi$/6 [Equation 2]

Tumor growth inhibition ratio (%)=[1−(final mean tumor volume in Asperphenin B-treated group)/(final mean tumor volume in control)]×100 [Equation 3]

Figure 8:
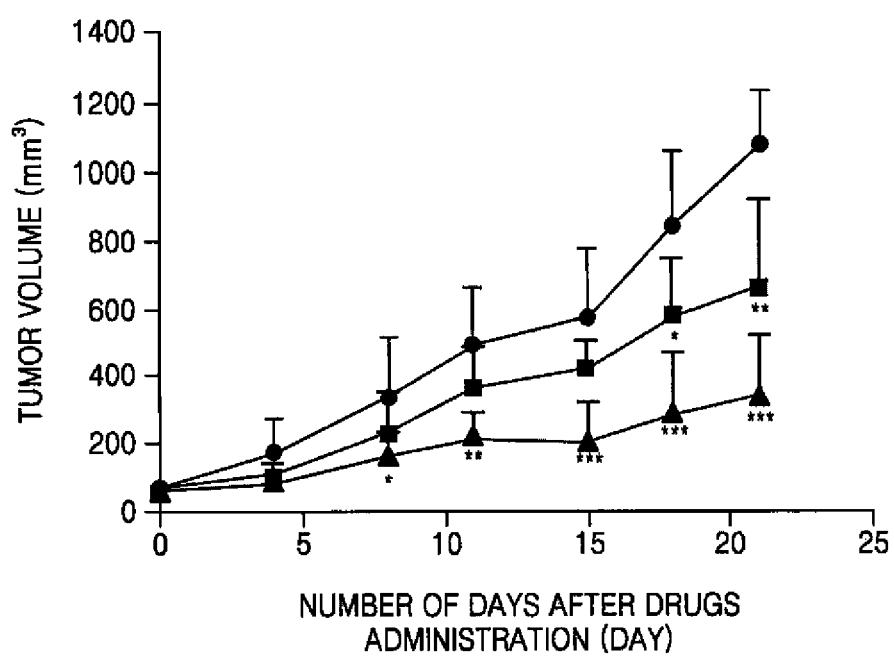
FIG. 8 is a graph showing the tumor volume ($mm^3$) of a mouse according to the number of days after 4 mg/kg or 8 mg/kg of Asperphenin B was administered into the mouse.

After administration of Asperphenin B, the tumor volume ($mm^3$) of the mouse according to the number of days are shown in FIG. 8 (●: control, ●: administration of 4 mg/kg of Asperphenin B, ▲: administration of 8 mg/kg of Asperphenin B, *: p<0.05, : p<0.01, *: p<0.005), and the tumor growth inhibition ratio calculated is shown in Table 9.

TABLE 9

| | Administration group | |
|---|---|---|
| | 4 mg/kg of Asperphenin B | 8 mg/kg of Asperphenin B |
| Inhibition ratio (%) | 38.9 | 68.7 |

As shown in Tables 8 and 9, the inhibition of tumor growth was observed in a compound concentration-dependent manner in the group administered with Asperphenin B.

Name of Depositary Authority: Collection of Microorganisms (International)

Accession Number: KCTC12688BP

Accession date: 20141013

The invention claimed is:

1. A pharmaceutical composition comprising a peptide compound represented by Formula 1 or the isomer, the derivative, or the pharmaceutically acceptable salt of the peptide compound, and an anticancer drug;

[Formula 1]

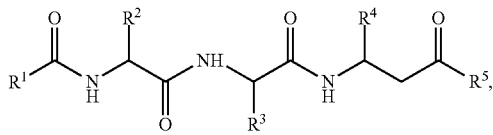

In Formula 1, $R^1$ is a substituted or unsubstituted $C_1$-$C_{20}$ alkyl group, a substituted or unsubstituted $C_1$-$C_{20}$ alkenyl group, or a substituted or unsubstituted $C_1$-$C_{20}$ alkynyl group, wherein $R^1$ is selectively unsubstituted or substituted with a hydroxyl group, $R^2$ and $R^3$ are each independently a $C_1$-$C_{20}$ alkyl group substituted with —C(=O)NH$_2$, $R^4$ is hydrogen, a hydroxyl group, a halogen group, a cyano group, a substituted or unsubstituted $C_1$-$C_{20}$ alkyl group, a substituted or unsubstituted $C_1$-$C_{20}$ alkoxy group, a substituted or unsubstituted $C_2$-$C_{20}$ alkenyl group, a substituted or unsubstituted $C_2$-$C_{20}$ alkynyl group, a $C_2$-$C_{20}$ alkylene oxide group, a substituted or unsubstituted $C_3$-$C_{30}$ cycloalkyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ heteroaryl group, or a combination thereof, and $R^5$ is a substituted or unsubstituted benzophenone.

2. The pharmaceutical composition of claim 1, wherein the peptide compound is represented by Formula 2:

[Formula 2]

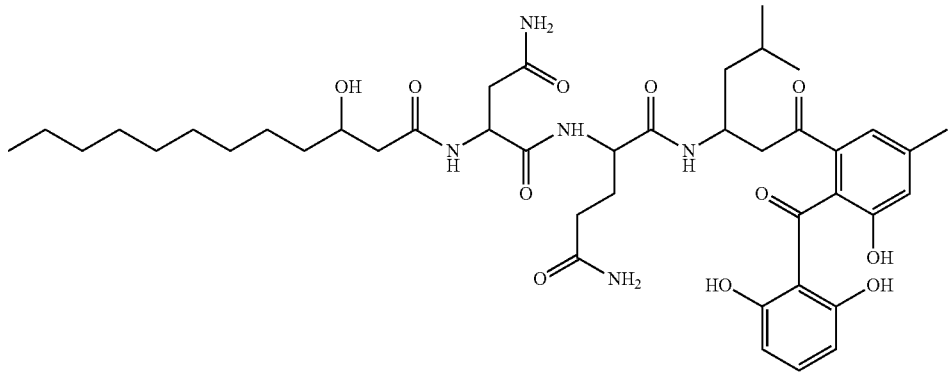

3. The pharmaceutical composition of claim 2, wherein the compound represented by Formula 2 is represented by Formula 3 or 4:

[Formula 3]

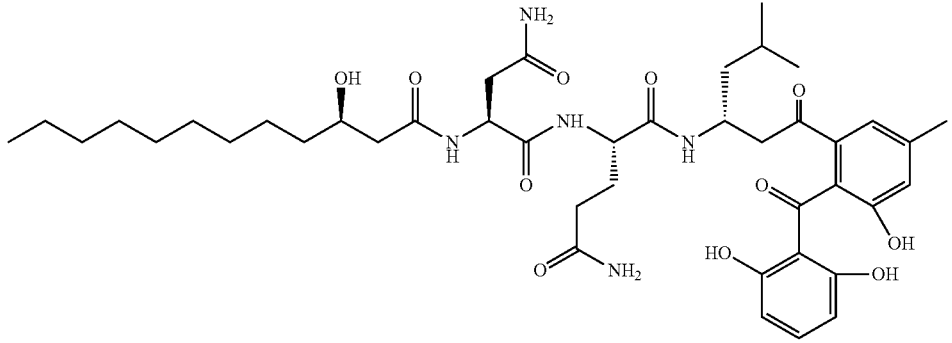

; and

[Formula 4]

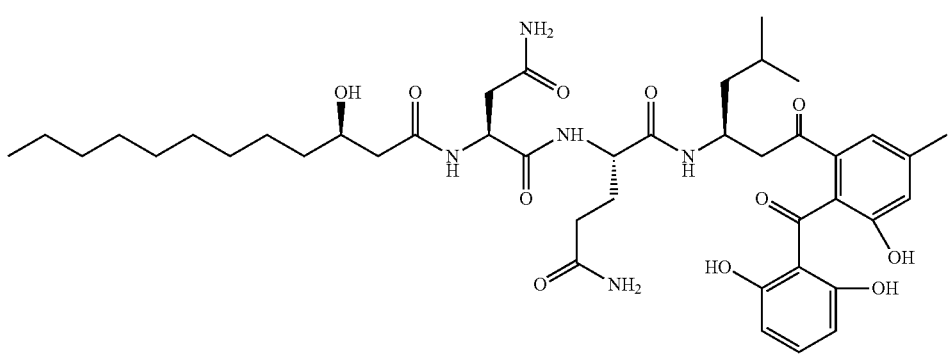

.

4. The pharmaceutical composition of claim 1, wherein the pharmaceutical composition is for preventing or treating cancer.

5. The pharmaceutical composition of claim 4, wherein the cancer is lung cancer, colon cancer, stomach cancer, liver cancer, or breast cancer.

6. The pharmaceutical composition of claim 1, wherein the anticancer drug is irinotecan, 5-fluorouracil, gemsitabin, etoposide, paclitaxel, or a combination thereof.

7. The pharmaceutical composition of claim 1, wherein the pharmaceutical composition is a single composition or a separate composition.

* * * * *